US 6,625,484 B2

(12) United States Patent
Köhler et al.

(10) Patent No.: US 6,625,484 B2
(45) Date of Patent: Sep. 23, 2003

(54) SIGNAL EVALUATION METHOD FOR DETECTING QRS COMPLEXES IN ELECTROCARDIOGRAM SIGNALS

(75) Inventors: Bert-Uwe Köhler, Berlin (DE); Reinhold Orglmeister, Berlin (DE)

(73) Assignee: Biotronik Mess- und Therapiegeräte GmbH & Co. Ingenieurbüro Berlin, Berlin (DE)

(*) Notice: Subject to any disclaimer, the term of this patent is extended or adjusted under 35 U.S.C. 154(b) by 0 days.

(21) Appl. No.: 09/803,679

(22) Filed: Mar. 12, 2001

(65) Prior Publication Data

US 2002/0058878 A1 May 16, 2002

(30) Foreign Application Priority Data

Mar. 10, 2000 (DE) .......................................... 100 11 733

(51) Int. Cl.[7] .............................................. A61B 5/042
(52) U.S. Cl. ....................................... 600/521; 128/901
(58) Field of Search .......................... 128/901; 600/509, 600/515–519, 521; 607/4–5, 9, 14, 17, 25–26

(56) References Cited

U.S. PATENT DOCUMENTS

| | | | |
|---|---|---|---|
| 5,309,917 A | | 5/1994 | Wang et al. |
| 5,766,227 A | * | 6/1998 | Nappholz et al. .............. 607/9 |
| 6,321,115 B1 | * | 11/2001 | Mouchawar et al. ........... 607/9 |

OTHER PUBLICATIONS

Peter Vary, "Digitale EKG–Triggerung ohne Multiplikationen", *Elektronik*, 1980, No. 10, pp. 61–66.
Gary M. Friesen et al; A Comparison of the Noise Sensitivity of Nine QRS Detection Algorithms. In: IEEE Transactions On Biomedical Engineering, vol. 37, No. 1, Jan. 1990, S.85–98.

* cited by examiner

Primary Examiner—Kennedy Schaetzle
Assistant Examiner—Kristen Droesch
(74) Attorney, Agent, or Firm—Browdy and Neimark, P.L.L.C.

(57) ABSTRACT

A signal evaluation method for detecting QRS complexes in electrocardiogram signals incorporates the following process steps:

sampling of the signal (4) and conversion to discrete signal values (x(n)) in chronological order, determining the sign of each signal value (x(n)), continuous checking of the signs of consecutive signal values (x(n)) for the presence of a zero crossing between two consecutive signal values (x(n)), determining the number (D(n)) of zero crossings in a defined segment (N) of the consecutive signal values (x(n)), and comparing the determined number of zero crossings (D(n)) to a defined threshold value, wherein an undershoot of the threshold value signifying the presence of a QRS complex (5, 6, 7) in the defined segment of the signal curve (4).

20 Claims, 3 Drawing Sheets

SIGNAL EVALUATION METHOD FOR DETECTING QRS COMPLEXES IN ELECTROCARDIOGRAM SIGNALS

BACKGROUND OF THE INVENTION

1. Field of the Invention

The present invention relates to a signal evaluation method for detecting QRS complexes in electrocardiogram (ECG) signals.

2. Background Art

Regarding the background of the invention, it can be stated that the automatic analysis of ECG signals is playing an increasingly larger role in perfecting the functionality of cardiac pacemakers and defibrillators. Newer models of implantable cardiac devices of this type accordingly also offer the capability to perform an ECG analysis. The detection of QRS complexes and R spikes in ECG signals plays an extremely important role in this context. This significance results from the many and diverse applications for the information concerning the time of occurrence of the QRS complex, for example when examining the heart rate variability, in the classification and data compression, and as the base signal for secondary applications. QRS complexes and R spikes that are not detected at all or detected incorrectly pose problems with respect to the efficiency of the processing and analysis phases following the detection.

A wide overview of known signal evaluation methods for detecting QRS complexes in ECG signals can be found in the technical essay by Friesen et al. "A Comparison of the Noise Sensitivity on Nine QRS Detection Algorithms" in IEEE Transaction on Biomedical Engineering, Vol. 37, No. 1, January 1990, pages 85–98. The signal evaluation algorithms presented there are based throughout on an evaluation of the amplitude, the first derivation of the signal, as well as its second derivation. For the presented algorithms, the essay distinguishes between those that perform an analysis of the amplitude and the first derivation, those that analyze only the first derivation, and those that take into consideration the first and second derivation. To summarize briefly, all algorithms check whether the given signal parameter exceeds or falls short of any predetermined thresholds, after which, if such an event occurs, the occurrence of additional defined events is checked based on a predefined pattern, and if certain criteria are fulfilled, the conclusion is drawn that an QRS complex is present.

Another aspect in the signal evaluation for detecting QRS complexes needs to be taken into account when methods of this type are implemented in implanted cardiac devices. In view of the natural limitations of these devices regarding their energy supply and computing capacity, it is important that the detection of QRS complexes can be performed with the simplest possible algorithms with the fewest possible mathematical operations on the basis of whole numbers instead of real numbers.

Signal processing methods from the fields of linear and non-linear filtering, wavelet transformation, artificial neural networks, and genetic algorithms have also been applied in the QRS detection. With large signal-noise distances and non-pathological signals, i.e., when good signal conditions are present, these evaluation methods produce reliable results. When no such conditions were present, the efficiency of the evaluation processes could drop drastically, which, of course, is not acceptable with regard to the reliable operation of a pacemaker.

SUMMARY OF THE INVENTION

Based on the described problems, the invention has as its object to present a signal evaluation method for detecting QRS complexes in ECG signals that can be used with a comparatively low computing capacity and also with problematic signal conditions while producing reliable detection results.

This object is met with the process steps according to the invention as follows:

- sampling of the signal and conversion to discrete signal values in chronological order,
- determining the sign of each signal value,
- continuous checking of the signs of consecutive signal values for the presence of a zero crossing between two consecutive signal values,
- determining the number of zero crossings in a defined segment of the consecutive signal values, and
- comparing the determined number of zero crossings to a defined threshold value, wherein an undershoot of the threshold value is significant for the presence of a QRS complex in the defined segment of the signal curve.

The core element of the inventive method is the application of a zero crossing count that is based on utilizing the morphology of the QRS complex. The QRS complex in the ECG signal is characterized by a relatively high-amplitude oscillation that markedly guides the signal curve away from the zero line of the electrocardiogram.

The frequency of this short oscillation lies within a range in which other signal components, such as the P and T waves, exert only minor influence and can be removed preferably by pre-filtering, e.g., high-pass or band-pass filtering. After suppression of these low-frequency signal components, signal fluctuations result around the zero line, due to higher-frequency noise, that dominate in the region where no QRS complex occurs. The QRS complex then appears in this signal context as a slow, high-amplitude oscillation of only short duration. The differentiation between a QRS complex and the other signal segments can thus be detected with a frequency measurement that can be described representatively, based on the discussed signal characteristics, by the number of zero crossings per defined evaluated segment. The zero crossing count produces a number that is nearly proportional to the given dominant frequency of the signal.

In lieu of pre-filtering the signal values to eliminate the P and T waves, the QRS complex may, in the inventive method, also be distinguished from the P and T waves by determining the duration or the moment of the significant absence of zero crossings within the ECG signal.

The method of detecting the QRS complex by counting zero crossings has proven robust with regard to noise interference and easy to implement with respect to the computing technology. In this respect it is particularly suitable for implementation in the real time analysis of ECG signal morphologies in cardiac pacemakers.

The previously mentioned high-pass filtering is performed preferably with a lower pass frequency of 18 Hz. In this manner the low-frequency components, such as the P and T waves, as well as a base line drift can be suppressed. Furthermore, the QRS complex thus becomes the signal component with the lowest frequency that dominates the signal during its occurrence.

To increase the signal-noise distance, provision may furthermore be made to square the signal values prior to checking them for zero crossings and prior to determining the number of zero crossings, while maintaining their signs. As a result, smaller signal values are weakened relative to larger signal values, which further improves the detectability of the QRS complex.

The same purpose is served by the preferred method characteristic of the addition of a high-frequency overlay signal b(n) to the high-pass filtered ECG signal that has been squared while maintaining its sign. With this measure the ECG signal is manipulated in such a way that a number of zero crossings is attained outside the QRS complex that is significantly easier to predict. With a properly chosen amplitude, in particular, the ECG signal may be processed such that the number of zero crossings outside the QRS complex is identical to the number of signal values in the respective evaluated segment. This means that a zero crossing takes place between each sampled value, unless a QRS signal complex is detected at that time. This effect is increased if the high pass is additionally replaced by a band pass, preferably with lower and upper pass frequencies of 18 Hz and 27 Hz, respectively. The value of the amplitude of the high-frequency overlay signal is preferably determined adaptively from a flowing determination of the average of the band-pass filtered and squared signal values over a defined averaging period.

In accordance with a further preferred embodiment of the inventive signal evaluation process, the threshold value of the number of zero crossings signifying a QRS complex is variably adjusted as an adaptive threshold of so-called quantiles of the frequency distribution of the number of zero crossings itself. More about this can be found in the description of the embodiment.

Lastly, in the detection of the QRS complex, the time of the occurrence of its R spike, too, is interesting from a cardiological point of view. This instant may be determined by determining the maximum of the band-pass filtered and squared signal values in a search interval around the instant at which the zero crossing count D(n) falls below the threshold value. The group delay of the band-pass filter must be subtracted from the time of the occurrence of the signal maximum to obtain the time of the occurrence of the R spike.

Lastly, an estimated useful signal strength and interfering signal strength is determined from the signal values as a further criterion for the presence of an interfering signal or useful signal, and a detection strength signifying the presence of an interfering signal or useful signal is determined therefrom.

The inventive method will be explained in greater detail below based on an embodiment, with the aid of the appended drawings in which:

DESCRIPTION OF THE PREFERRED EMBODIMENT

Figure 1:
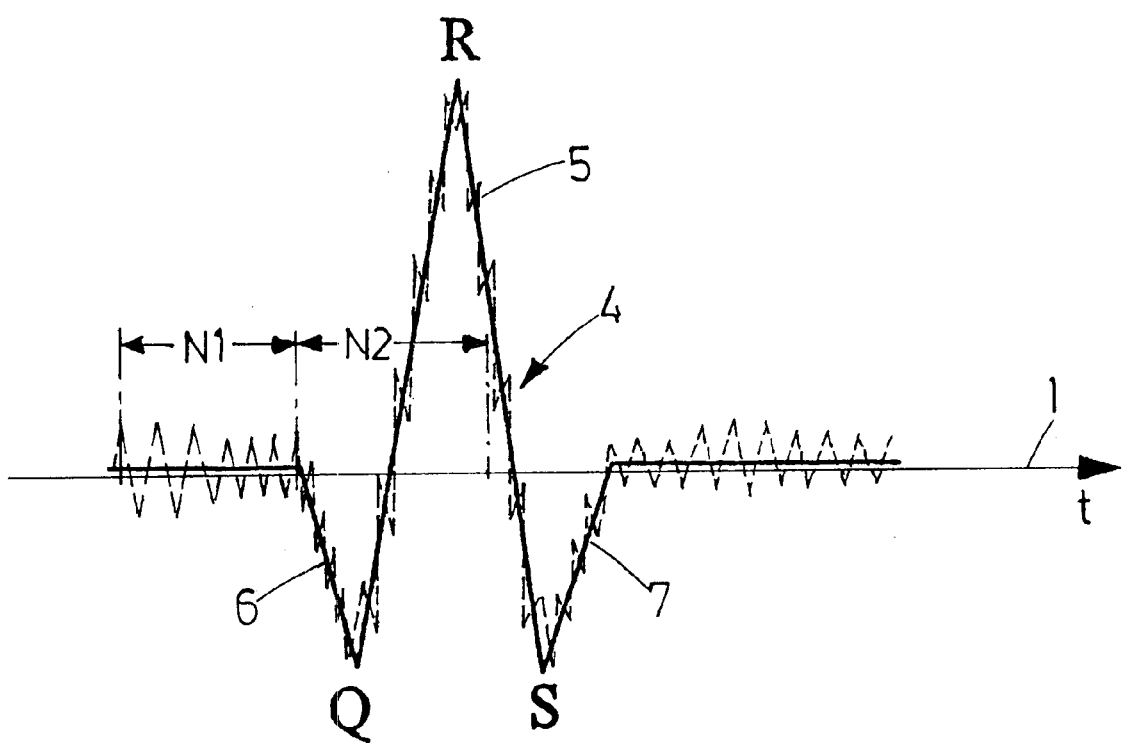
FIG. 1 shows a highly schematic presentation of the signal curve of a QRS complex in an ECG signal.

As is apparent from FIG. 1, an idealized QRS complex consists of a relatively high-amplitude oscillation that initially guides the ECG signal, in the Q spike, away from the zero line 1 in a negative direction. Afterwards the ECG signal is guided, in the R spike, into the positive range with a steep rise and with a subsequent steep drop back into the negative range while forming the S spike.

In reality the ECG signal is accompanied by a certain level of noisiness, as indicated in FIG. 1 by the dashed signal curve. If this noisy signal is now sampled and converted into discrete signal values in chronological order, the sign of each signal value can be determined and a check can be performed as to whether a zero crossing of the ECG signal though the zero line 1 has taken place between these signal values. Outside the QRS complex a high number of zero crossings occurs in a defined segment N1, whereas a much lower number of zero crossings is detected during sampling of a segment N2 in the QRS complex. The count of the number of zero crossings may thus be used to detect a QRS complex.

The ECG signal is sampled and converted into discrete signal values x(n) in chronological order. The sampling rate may be f=360 Hz, for example, i.e., the ECG signal is converted into a sequence of 360 measuring values per second.

The detailed sequence of the inventive evaluation method will now be explained in more detail based on FIG. 2. According to that structural diagram, the sampled ECG signal x(n) is subjected, on the input side, to a band-pass filtering that serves to remove all signal components that do not belong to the QRS complex. This includes the P and T waves, as well as high-frequency noise that may originate, for example, from the bioelectrical muscle activity. This furthermore suppresses the base line drift and moves the ECG to the zero line 1. The applied filter BP is non-recursive, linear-phase and has a band-pass characteristic with the pass frequencies $f_{g1}$=18 Hz and $F_{g2}$=27 Hz, as well as the limiting cutoff frequencies $f_{g1}$=2 Hz and $f_{g2}$=50 Hz. The filter order is N=200. The group delay of the band-pass filter BP accordingly corresponds to 100 sampling values and must be taken into consideration when determining the time of the occurrence of the QRS complex. The blocking attenuation of the filter is approximately 80 dB.

The signal values $x_f(n)$ attained in this manner are subsequently squared in a squaring step QS according to the following relation while maintaining the signs of the given signal values:

$$x_{fq}(n) = \text{sign}[x_f(n)] |x_f(n)|^2$$

In an adding phase 2, a high-frequency sequence b(n) with a low amplitude that may be described as follows is subsequently overlaid to the band-pass filtered and squared ECG signal:

$$b(n) = (-1)^n K(n)$$

wherein K(n)>0. Adding is sequence b(n) changes the number of zero crossings per segment. The upper limit of the number of zero crossings is the number N of the sampling values of the segment. With this sequence b(n) the number of zero crossings is increased to this maximum number in the non-QRS segments, whereas the (lower) number of zero crossings is maintained in the QRS complex. To attain this goal, a suitable value for the coefficients K(n) is adaptively estimated from the signal values $X_{fq}(n)$. The band-pass filtered and squared signals are determined flowingly for this purpose over a defined averaging interval of P sampling values according to the following equation:

$$\langle |x_{jq}|\rangle(n) = 1/P \cdot \sum_{i=0}^{P-1} |x_{fq}(n-i)|$$

wherein P=4·(number of sampling values per second).

Empirically, the following relation results for K(n):

$$K(n)=9 \cdot \langle |x_{fq}|\rangle(n)$$

The averaging time essentially determines the adaptation speed of this estimate and both, averaging segments that are too short, as well as averaging segments that are too long may impact the effectiveness of the signal evaluation method. During the occurrence of QRS complexes the adaptation is paused since the sequence b(n) is intended to only influence the zero crossings during the non-QRS segments.

Figure 2:
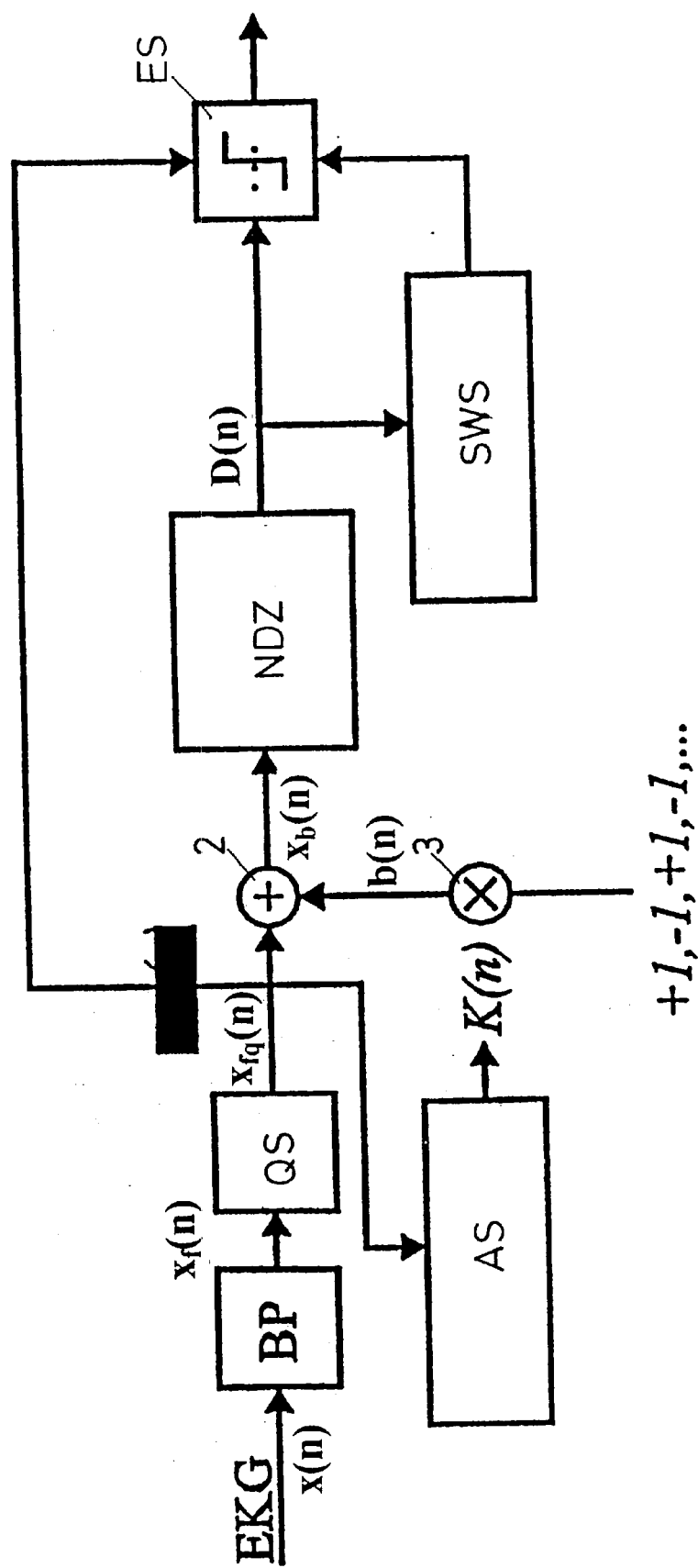
FIG. 2 shows a structural diagram of the inventive signal evaluation method for detecting QRS complexes in ECG signals.

In FIG. 2, the process complex that pertains to the determination of the coefficients K(n) has been marked as AS. The multiplication of the basic function—indicated in FIG. 2 as a kind of "flip flop function" with "+1, −1, +1, −1, ..."—with the amplitude K(n) has been indicated in the form of the multiplication step 3.

The above discussed signal values are now subjected to the actual zero crossing count NDZ. Counting the zero crossings is principally performed per segment according to the following relation:

$$D(n) = \sum_{i=0}^{N-1} d(n-i)$$

with N indicating the segment length. Furthermore, the following applies:

$$d(n)=\tfrac{1}{2}|\mathrm{sign}[x_b(n)]-\mathrm{sign}[x_b(n-1)]|.$$

If d(n)=1, this means "zero crossing detected", d(n)=0 means "no zero crossing detected." In this manner a high number of zero crossings per segment results for high frequencies and accordingly fewer for low frequencies.

From a signal technology point of view, counting the zero crossings essentially corresponds to a low-pass filtering; in practice counting the zero crossings may be implemented with a filter having a square-pulse response, i.e., the filter pulse response $a_i$=1 with i=0 ... N−1 produces the number of zero crossings D(n). The advantage of this filter results from the implementation with N−1 shift operations, which is favorable from a computing point of view, and feedback without multiplication. The filter function is, in fact, defined as follows:

$$H(z) = \sum_{i=0}^{N-1} z^{-1} = (1-z^{-(N-1)})/(1-z^{-1})$$

A further advantage of this implementation lies in the fact that the number of zero crossings takes exclusively whole-number values, the range of which is determined by the segment length N. This feature can be advantageously utilized in the subsequent decision phase ES. The filter order N furthermore significantly influences the robustness of the sign evaluation method with respect to noise. Larger filter orders increase the robustness, however, filters that are too long, on the other hand, due to the prolonged averaging interval, may lead to false-negative detection errors ("false negative" means that even though a QRS complex is present in the ECG signal, it was not detected.) In the present embodiment, the filter order N=10 is used.

The threshold value of the number of zero crossings that is significant for the detection of a QRS complex is determined by comparison with an adaptive threshold. The latter is determined from the average of the 0.1 and 0.5 quantiles of the frequency distribution f(m) of D(n). The statistical size "quantile" is used because it has a greater robustness, compared to average and variance, with respect to statistic freak values. In the present case it is very easy to calculate, as the signal values can take only whole-number values between 0≦D(n)≦N. The frequency distribution f(m) with 0≦m≦N is determined adaptively in two steps, namely:

$$f_n^*(m)=(1-\lambda)f_{n-1}(m)$$

and $$f_n[D(n)]=f_n^*[D(n)]+\lambda$$

wherein a memory factor 0<λ<1 is used. For the numerical example briefly shown at the end of this description, this memory factor was selected as λ=0.01. It is now easy to determine from the frequency distribution the quantiles and from them, in the manner described above, the adaptive threshold. If D(n) is below the threshold, a QRS complex has been detected, otherwise not. In FIG. 2 the process segment of the threshold estimation has been marked with SWS.

In other respects, the band-pass filtered and squared signal $x_{fq}(t)$ is used to determine the exact time of the occurrence of the R spike of a QRS complex. For this purpose the maximum in this signal is searched in a search interval around the starting point of a QRS complex, the occurrence of which is set as the time of the occurrence of the R spike.

Simultaneous with the actual detection of QRS complexes and to determine the time of the occurrence of the R spike, two additional variables are estimated in the evaluation process for the purpose of evaluating the signal, namely the useful signal strength $P_{QRS}$ and the noise signal strength $P_{Noise}$. One of the two variables is updated with each detected result. When a QRS complex is detected, the estimated useful signal strength is updated, otherwise the estimated interfering signal strength is updated. For this purpose the value $|x_{fq}(t)|_{max}$ is used in a suitable interval around the instant at which the number of zero crossings D(n) falls below the threshold value, with one exponential windows used in each case in the present implementation. This means the following derivation applies for the estimated useful and interfering signal strengths:

$$P_{QRS}(i+1)=(1-\lambda_{QRS}) \cdot P_{QRS}(i)+\lambda_{QRS} \cdot |x_{fq}(t)|_{max}$$

in case of a QRS complex $$P_{Noise}(i+1)=(1-\lambda_{Noise}) \cdot P_{Noise}(i)+\lambda_{Noise} \cdot |x_{fq}(t)|_{max}$$

in case of noise.

The memory factors λ in the above two equations were selected as follows:

$$\lambda_{QRS}=0.5$$

and $$\lambda_{Noise}=0.01.$$

Lastly, a detection strength is calculated from the estimated signal strengths according to the following relation, the value of which provides information as to whether an event that would normally be qualified as a QRS complex is indeed a useful signal that should be attributed to a QRS complex for the signal evaluation method. The detection strength is calculated as follows:

$$DS=(|x_{fq}(t)|_{max}-P_{Noise})/(P_{QRS}-P_{Noise})$$

In the present example a detected peak is classified as an interfering signal if the detection strength is less than 0.01. In that case the interfering signal strength is updated. Otherwise it is a QRS complex, after which the useful signal strength is updated accordingly.

Lastly, a time window of 75 ms is used in the signal evaluation. If multiple QRS complexes are detected within this time window, only the first complex is evaluated and the other complexes are extracted. This relatively short refractory time was selected to ensure a swift resumption of the normal detection in case of false-positive detections of a QRS complex, and to thus reduce false-negative recognition errors.

The inventive signal evaluation method as described in detail above was tested and validated with the aid of a database with the designation "MIT/BIH Arrhythmia Data Base" that is sold commercially for test purposes. This database contains 48 two-channel ECG signals with a length of approximately 30 minutes each. These ECG signals are ranged into classes, so that the location of the QRS complexes is known.

The signal evaluation method was performed on a personal computer, with a frequency f used as the sampling rate. To evaluate the efficiency of the present method, the so-called sensitivity Se and specificity +P were determined according to the following condition:

$$Se=TP/(TP+FN) \text{ sensitivity}$$

$$+P=TP/(TP+FP) \text{ specificity}$$

wherein the number of correctly detected QRS complexes is included as TP, the number of false-negative detections is included as FN, and that of the false-positive detections is included as FP. A QRS complex was assumed detected correctly if it was detected within a time window of +/−75 ms around the actual location of the time of its occurrence. The results of this simulation example are listed in the appended Table 1. From this table it can be seen that the sensitivity Se and specificity +P were significantly higher than 99% for the large majority of data sets—the so-called "tapes"—and in some instances exactly 100%. Only in very few cases of very noisy signals, such as in tapes No. 105 and 108 were these values lower, however, still high enough for good results to be obtained there as well.

Figure 3:
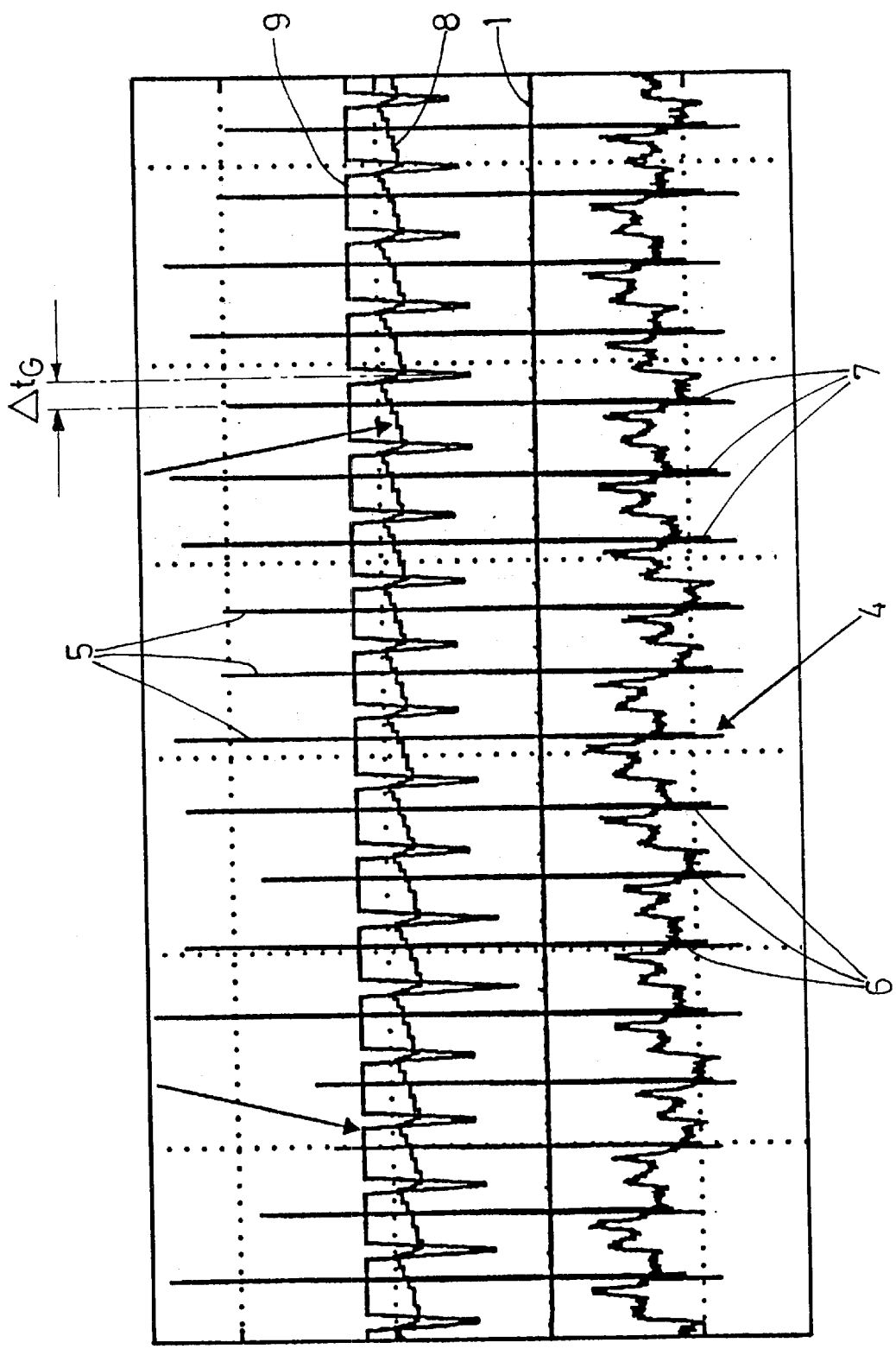
FIG. 3 shows typical signal curves as they occur with the application of the inventive signal evaluation method according to FIG. 2.

The simulation example is also shown graphically in FIG. 3 by way of example. The signal curve 4, for example, reflects the actual ECG signal. It clearly shows the R spike 5, the immediately adjacent Q and S spikes 6, 7 are only implied.

Also entered is the adaptive threshold 8 for distinguishing between QRS and non-QRS segments. Based thereon, the curve 9 reflects the course of the number of zero crossings of the ECG signal values. It is apparent how, after the occurrence of a QRS complex, the number of zero crossings breaks in with a delay $t_G$ that corresponds to the group delay time in the sampling and filtering of the ECG signal. This is reflected in the downward pointing spikes in the curve 9. Synchronously, the threshold value 8 is adapted after the occurrence of a QRS complex, as is apparent from the saw-tooth shaped curve of the threshold value 8 in FIG. 3.

TABLE 1

Results of the QRS detection with count of zero crossings on the MIT/BIH Arrhythmia Data Base

| Tape No. | Channel | TP | FN | FP | Se (%) | +P (%) |
|---|---|---|---|---|---|---|
| 100 | MLII | 1901 | 1 | 0 | 99.95 | 100.00 |
| 101 | MLII | 1522 | 1 | 8 | 99.93 | 99.48 |
| 102 | V5 | 1808 | 13 | 13 | 99.29 | 99.29 |
| 103 | MLII | 1728 | 1 | 0 | 99.94 | 100.00 |
| 104 | V5 | 1839 | 18 | 18 | 99.03 | 99.03 |
| 105 | MLII | 2151 | 4 | 37 | 99.81 | 98.31 |
| 106 | MLII | 1691 | 5 | 9 | 99.71 | 99.47 |
| 107 | MLII | 1776 | 8 | 7 | 99.55 | 99.61 |
| 108 | MLII | 1448 | 32 | 30 | 97.84 | 97.97 |
| 109 | MLII | 2077 | 22 | 3 | 98.95 | 99.86 |
| 111 | MLII | 1773 | 3 | 12 | 99.83 | 99.33 |
| 112 | MLII | 2110 | 1 | 9 | 99.95 | 99.58 |
| 113 | MLII | 1505 | 1 | 5 | 99.93 | 99.67 |
| 114 | V5 | 1604 | 0 | 6 | 100.00 | 99.63 |
| 115 | MLII | 1636 | 1 | 0 | 99.94 | 100.00 |
| 116 | MLII | 1997 | 20 | 4 | 99.01 | 99.80 |
| 117 | MLII | 1283 | 1 | 2 | 99.92 | 99.84 |
| 118 | MLII | 1916 | 0 | 2 | 100.00 | 99.90 |
| 119 | MLII | 1661 | 0 | 0 | 100.00 | 100.00 |
| 121 | MLII | 1538 | 22 | 33 | 98.59 | 97.90 |
| 122 | MLII | 2053 | 1 | 0 | 99.95 | 100.00 |
| 123 | MLII | 1269 | 0 | 5 | 100.00 | 99.61 |
| 124 | MLII | 1365 | 2 | 4 | 99.85 | 99.71 |
| 200 | MLII | 2165 | 3 | 27 | 99.86 | 98.77 |
| 201 | MLII | 1520 | 1 | 84 | 99.93 | 94.76 |
| 202 | MLII | 1870 | 1 | 13 | 99.95 | 99.31 |
| 203 | MLII | 2437 | 44 | 38 | 98.23 | 98.46 |
| 205 | MLII | 2195 | 6 | 0 | 99.73 | 100.00 |
| 207 | MLII | 1586 | 6 | 113 | 99.62 | 93.35 |
| 208 | MLII | 2419 | 18 | 8 | 99.26 | 99.67 |
| 209 | MLII | 2518 | 0 | 6 | 100.00 | 99.76 |
| 210 | MLII | 2200 | 4 | 6 | 99.82 | 99.73 |
| 212 | MLII | 2284 | 1 | 7 | 99.96 | 99.69 |
| 213 | MLII | 2672 | 28 | 26 | 98.96 | 99.04 |
| 214 | MLII | 1876 | 2 | 12 | 99.89 | 99.36 |
| 215 | MLII | 2794 | 1 | 0 | 99.96 | 100.00 |
| 217 | MLII | 1843 | 2 | 8 | 99.89 | 99.57 |
| 219 | MLII | 1773 | 0 | 1 | 100.00 | 99.94 |
| 220 | MLII | 1693 | 1 | 0 | 99.94 | 100.00 |
| 221 | MLII | 2004 | 16 | 17 | 99.21 | 99.16 |
| 222 | MLII | 2116 | 0 | 6 | 100.00 | 99.72 |
| 223 | MLII | 2199 | 0 | 2 | 100.00 | 99.91 |
| 228 | MLII | 1701 | 2 | 55 | 99.88 | 96.87 |
| 230 | MLII | 1859 | 0 | 15 | 100.00 | 99.20 |
| 231 | MLII | 1278 | 0 | 0 | 100.00 | 100.00 |
| 232 | MLII | 1485 | 0 | 22 | 100.00 | 98.54 |
| 233 | MLII | 2550 | 11 | 0 | 99.57 | 100.00 |
| 234 | MLII | 2289 | 2 | 0 | 99.91 | 100.00 |
| Total: | | 90977 | 306 | 673 | 99.66 | 99.27 |

What is claimed is:

1. A signal evaluation method for detecting QRS complexes in electrocardiogram (ECG) signals (4), comprising the following process steps:

sampling of the signal (4) and conversion to discrete signal ECG values (x(n)) in chronological order, determining the sign of each ECG signal value ($x_f(n)$), continuous checking of the signs of consecutive ECG signal values ($x_f(n)$) for a presence of a zero crossing between two consecutive signal values ($x_f(n)$), determining a number (D(n)) of zero crossings in a defined segment (N) of the consecutive ECG signal values ($x_f(n)$), and comparing the determined number of zero crossings (D(n)) to a defined threshold value, wherein an undershoot of the threshold value is significant for a presence of a QRS complex (5, 6, 7) in a defined segment of the signal curve (4).

2. A signal evaluation method according to claim 1, wherein after the sampling, the ECG signal values (x(n)) are subjected to a high-pass filtering.

3. A signal evaluation method according to claim 1, wherein after the sampling, the ECG signal values (x(n)) are subjected to a band-pass filtering (BP).

4. A signal evaluation method according to claim 3, wherein the lower and upper pass frequencies ($f_{g1}$, $f_{g2}$) of the band pass filtering (BP) are approximately 18 Hz and 27 Hz, respectively.

5. A signal evaluation method for detecting QRS complexes in electrocardiogram (ECG) signals (4), comprising the following process steps:

sampling of the signal (4) and conversion to discrete signal ECG values (x(n)) in chronological order, determining the sign of each ECG signal value ($x_j(n)$), continuous checking of the signs of consecutive ECG signal values ($x_j(n)$) for a presence of a zero crossing between two consecutive signal values ($x_j(n)$), determining a number (D(n)) of zero crossings in a defined segment (N) of the consecutive ECG signal values ($x_j(n)$), and comparing the determined number of zero crossings (D(n)) to a defined threshold value, wherein an undershoot of the threshold value is significant for a presence of a QRS complex (5, 6, 7) in a defined segment of the signal curve (4), wherein the signal values ($x_j(n)$) are squared prior to checking them for zero crossings and determining the number of zero crossings (D(n)), while maintaining their respective signs.

6. A signal evaluation method according to claim 5, wherein a maximum of the band-pass filtered and squared ECG signal values ($x_{fq}(n)$) is determined in a search interval around a starting point of a QRS complex (5, 6, 7) to determine the time of an occurrence of the R spike (5).

7. A signal evaluation method according to claim 5, wherein after the sampling, the ECG signal values (x(n)) are subjected to a high-pass filtering.

8. A signal evaluation method according to claim 5, wherein after the sampling, the ECG signal values (x(n)) are subjected to a band-pass filtering (BP).

9. A signal evaluation method according to claim 8, wherein the lower and upper pass frequencies ($f_{g1}$, $f_{g2}$) of the band pass filtering (BP) are approximately 18 Hz and 27 Hz, respectively.

10. A signal evaluation method according to claim 5, wherein a high-frequency overlay signal (b(n)) with an amplitude (K(n)) that is low in comparison to an amplitude of the QRS complex (5, 6, 7) is added to the band-pass filtered and squared ECG signal values ($x_{fq}(n)$) prior to checking for zero crossings and determining the number of zero crossings (D(n)).

11. A signal evaluation method according to claim 10, wherein a value of the amplitude (K(n)) of the high-frequency overlay signal (b(n)) is adaptively determined from a flowing determination of the average of the band-pass filtered and squared ECG signal values ($x_{fq}(n)$) over a defined averaging period (P).

12. A signal evaluation method according to claim 10, wherein the addition of the high-frequency overlay signal (b(n)) is paused when a QRS complex (5, 6, 7) is detected.

13. A signal evaluation method for detecting QRS complexes in electrocardiogram (ECG) signals (4), comprising the following process steps:

sampling of the signal (4) and conversion to discrete signal ECG values (x(n)) in chronological order, determining the sign of each ECG signal value ($x_j(n)$), continuous checking of the signs of consecutive ECG signal values ($x_j(n)$) for a presence of a zero crossing between two consecutive signal values ($x_j(n)$), determining a number (D(n)) of zero crossings in a defined segment (N) of the consecutive ECG signal values ($x_j(n)$), and comparing the determined number of zero crossings (D(n)) to a defined threshold value, wherein an undershoot of the threshold value is significant for a presence of a QRS complex (5, 6, 7) in a defined segment of the signal curve (4), wherein the threshold value of the number of zero crossings signifying a QRS complex (5, 6, 7) is variably adjusted as an adaptive threshold from quantiles of a frequency distribution (f(m)) of the number of zero crossings itself.

14. A signal evaluation method according to claim 13, wherein after the sampling, the ECG signal values (x(n)) are subjected to a high-pass filtering.

15. A signal evaluation method according to claim 13, wherein after the sampling, the ECG signal values (x(n)) are subjected to a band-pass filtering (BP).

16. A signal evaluation method according to claim 15, wherein the lower and upper pass frequencies ($f_{g1}$, $f_{g2}$) of the band pass filtering (BP) are approximately 18 Hz and 27 Hz, respectively.

17. A signal evaluation method for detecting QRS complexes in electrocardiogram (ECG) signals (4), comprising the following process steps:

sampling of the signal (4) and conversion to discrete signal ECG values (x(n)) in chronological order, determining the sign of each ECG signal value ($x_j(n)$), continuous checking of the signs of consecutive ECG signal values ($x_j(n)$) for a presence of a zero crossing between two consecutive signal values ($x_j(n)$), determining a number (D(n)) of zero crossings in a defined segment (N) of the consecutive ECG signal values ($x_j(n)$), and comparing the determined number of zero crossings (D(n)) to a defined threshold value, wherein an undershoot of the threshold value is significant for a presence of a QRS complex (5, 6, 7) in a defined segment of the signal curve (4), wherein an estimated useful signal strength ($P_{QRS}$) and an estimated interfering signal strength ($P_{Noise}$) are determined from the signal values ($x_{fq}(n)$) and a detection strength (DS) signifying the presence of at least one of an interference signal and useful signal is determined from same.

18. A signal evaluation method according to claim 17, wherein after the sampling, the ECG signal values (x(n)) are subjected to a high-pass filtering.

19. A signal evaluation method according to claim 17, wherein after the sampling, the ECG signal values (x(n)) are subjected to a band-pass filtering (BP).

20. A signal evaluation method according to claim 19, wherein the lower and upper pass frequencies ($f_{g1}$, $f_{g2}$) of the band pass filtering (BP) are approximately 18 Hz and 27 Hz, respectively.

* * * * *